United States Patent [19]

Erhardt et al.

[11] Patent Number: 4,737,511

[45] Date of Patent: Apr. 12, 1988

[54] CARDIOTONIC IMIDAZOLYLPHENYLPYRROL-2-ONES

[75] Inventors: Paul W. Erhardt, Long Valley; Alfred A. Hagedorn, III, Edison, both of N.J.; John W. Lampe, Berlin, Fed. Rep. of Germany

[73] Assignee: Schering A.G., Berlin, Fed. Rep. of Germany

[21] Appl. No.: 925,956

[22] Filed: Nov. 3, 1986

[51] Int. Cl.$^4$ .................. A61K 31/415; C07D 403/00; C07D 487/00

[52] U.S. Cl. .................................. 514/394; 548/336; 548/327; 514/397

[58] Field of Search ................ 548/336, 327; 514/397, 514/394

[56] References Cited

U.S. PATENT DOCUMENTS 4,259,345  3/1981  Cross et al. ..................... 548/336

Primary Examiner—Henry R. Jiles
Assistant Examiner—Robert C. Whittenbaugh
Attorney, Agent, or Firm—Elizabeth A. Bellamy; John L. White; I. William Millen

[57] ABSTRACT

Novel imidazolylphenylpyrrol-2-ones are described as having cardiovascular properties especially as cardiotonic agents in the treatment of congestive heart failure. Pharmaceutical formulations containing such compounds are also described.

13 Claims, No Drawings

CARDIOTONIC IMIDAZOLYLPHENYLPYRROL-2-ONES

FIELD OF INVENTION

This invention relates to novel imidazolylphenylpyrrol-2-ones and their use as cardiovascular agents. More particularly, this invention relates to 1,5- and 1,3-dihydro-[(1H-imidazol-1-yl)phenyl]-2H-pyrrol-2-ones and their pharmaceutically acceptable acid addition salts, to pharmaceutical compositions containing them as active ingredients and to the method of using them as cardiovascular agents, more especially as cardiotonic agents in the treatment of congestive heart failure.

GENERAL DESCRIPTION OF THE INVENTION COMPOSITION-OF-MATTER ASPECT

In its composition-of-matter aspect this invention relates to novel imidazolylphenylpyrrol-2-ones and their pharmaceutically acceptable acid addition salts. Particularly, this invention relates to the novel compounds defined by the following Formulae I and II.

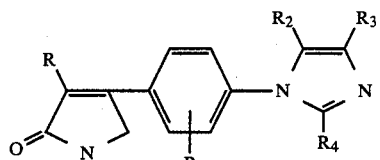

and

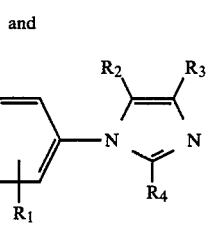

wherein
R is lower alkyl;
$R_1$, $R_2$, $R_3$ and $R_4$ are the same or independently hydrogen or lower alkyl, or $R_2$ and $R_3$ when taken together form a benzene ring;
or a pharmaceutically acceptable acid addition salt thereof;
with the proviso that R cannot be tertiary butyl.

As used herein the term lower alkyl represents a straight or branched chain of from 1 to 4 carbon atoms, as, for example, methyl, ethyl, propyl, isopropyl, butyl, isobutyl, sec-butyl and tertiary butyl.

Also contemplated as part of this invention are the pharmaceutically acceptable acid addition salts of the compounds of Formulae I and II. These acid addition salts may be formed with inorganic or organic acids. Illustrative but not restrictive examples of such acids include hydrochloric, hydrobromic, sulfuric, phosphoric, acetic, benzoic, methanesulfonic and 2-hydroxyethanesulfonic acid. In comparison to the parent compounds these salts usually exhibit greater solubility in water and hydrophilic organic solvents.

Preferred classes of compounds embodied by this invention are those of the above general Formulae I and II having one of the following characteristics:
 (a) R is lower alkyl,
 (b) $R_1$ is hydrogen,
 (c) $R_4$ is hydrogen or lower alkyl,
 (d) $R_2$ and $R_3$ are hydrogen.

The more preferred compounds of this invention are those containing all the foregoing a-d characteristics.

The compounds which follow are some of those which serve to exemplify the various composition-of-matter aspects of the invention described herein.
 (a) 3-Ethyl-1,5-dihydro-4-[4-(2-methyl-1H-imidazol-1-yl)phenyl]-2H-pyrrol-2-one.
 (b) 1,5-Dihydro-3-methyl-4-[4-(2-methyl-1H-imidazol-1-yl)phenyl]-2H-pyrrol-2-one.
 (c) 1,5-Dihydro-4-[4-(1H-imidazol-1-yl)phenyl]-3-methyl-2H-pyrrol-2-one.
 (d) 3-Ethyl-1,5-dihydro-4-[4-(1H-imidazol-1-yl)phenyl]-2H-pyrrol-2-one.
 (e) 1,5-Dihydro-3-(1-methylethyl)-4-[2-methyl-4-(2,4,5-trimethyl-1H-imidazol-1-yl)phenyl]-2H-pyrrol-2-one.
 (f) 4-[4-(2-Butyl-4-propyl-1H-imidazol-1-yl)-3-ethylphenyl]-1,5-dihydro-3-(2-methylpropyl)-2H-pyrrol-2-one.
 (g) 3-Ethyl-4-[4-(2-ethyl-1H-benzimidazol-1-yl) -3-methylphenyl]-1,5-dihydro-2H-pyrrol-2-one.
 (h) 1,3-Dihydro-4-[4-(1H-imidazol-1-yl)phenyl]-5-methyl-2H-pyrrol-2-one.
 (i) 1,3-Dihydro-5-methyl-4-[4-(2-methyl-1H-imidazol-1yl)phenyl]-2H-pyrrol-2-one.
 (j) 5-Ethyl-4-[4-(2-ethyl-1H-imidazol-1-yl)phenyl]-1,3-dihydro-2H-pyrrol-2-one.
 (k) 4-[4-(2-Butyl-4-methyl-1H-imidazol-1-yl)phenyl]-1,3-dihydro-5-(1-methylethyl)-2H-pyrrol-2-one.
 (l) 5-Ethyl-1,3-dihydro-4-[4-(2-methyl-1H-imidazol-1yl)phenyl]-2H-pyrrol-2-one.
 (m) 5-Ethyl-1,3-dihydro-4-[4-(1H-imidazol-1-yl)phenyl]-2H-pyrrol-2-one.

Process Aspect

In general the compounds of Formula I of this invention may be prepared as follows in Scheme A.

Scheme A

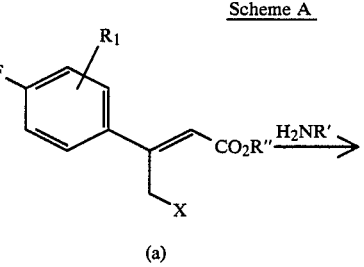

(a)

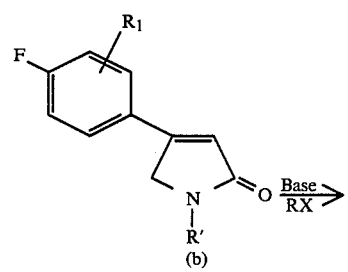

(b)

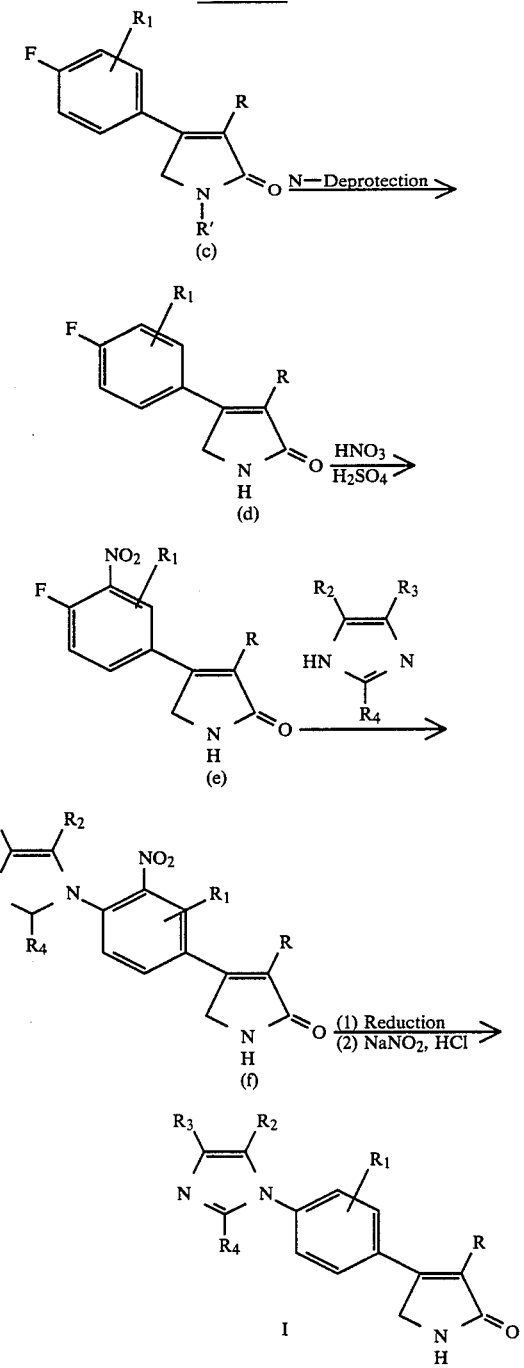

Wherein X is bromine, chlorine or iodine; R and R" are independently lower alkyl; R' is lower alkyl, aralkyl, aryl or substituted aryl wherein R' is suitable for use as a temporary protecting group for nitrogen; and $R_1$, $R_2$, $R_3$ and $R_4$ are independently H or lower alkyl.

Cyclization to form pyrrolones (b) can be accomplished conveniently in a one-step process from the substituted cinnamate esters (a) by employing a 2 to 5 fold excess of a suitably protected amine ($H_2NR'$) such that the amine also serves as a base to trap HX formed during the reaction. The protecting groups (R') for the amine are those known in the art which are stable to the basic conditions employed in the next step and which are subsequently removed by either reductive, oxidative or acidic treatment. Preferred choices for R' are benzyl and para-methoxyphenyl, the latter being the most preferred. The cinnamate ester (a) and protected amine can be combined in any common organic solvent, most generally lower alkanols. It is particularly preferred to employ an alcohol which corresponds to the R" moiety present in the cinnamate ester; for example, ethanol is preferred when R" is ethyl. The reaction medium is stirred from 1 to 48 hours at temperatures between 25° C. and 100° C. depending upon the reactivity of the protected amine and the choice of solvent. Typically, the reactions are stirred for 24 hours at room temperature. The cyclized product (b) may be isolated by standard procedures known in the art; for example, by direct precipitation or crystallization from the reaction medium, by removal of solvent followed by aqueous washing and extraction into organic phases, or standard chromatographic purification. The cyclized compounds (b) are typically obtained in greater than 50% yields.

Alkylation of (b) can be accomplished by treatment with an organic base followed by an alkyl halide (RX). In general, one equivalent to 1.1 equivalents of an organic base such as lithium diisopropylamide is employed in a non-protic solvent such as tetrahydrofuran. The specifically indicated base/solvent pair can be generated conveniently from diisopropylamine and n-butyllithium under a nitrogen atmosphere and at low temperature, eg. −60° C. The pyrrolone (b) is added at this temperature and the mixture typically stirred for 5 min. to 1 hour before the temperature is raised slowly to between −10° C. and 25° C., at which it is stirred for 30 minutes to 2 hours. The reaction mixture is then cooled to between −80° C. and −50° C. and 1 to 1.1 equivalents of an alkyl halide (RX), preferably the alkyl iodide (RI) is slowly added. The temperature is gradually raised to between −20° C. and −30° C. and the reaction mixture stirred for 6 to 24 hours. The major products from such alkylations have the alkyl group (R) attached at the pyrrolone 3-position, that is, with the regiochemistry indicated in (c). However, regioisomers resulting from alkylation at other positions can be obtained as side products, as can dialkylated products. Purification typically involves standard partitioning methods such as acidification of the reaction medium with 4 N HCl followed by extraction with an organic solvent such as methylene chloride. In many instances the residues after evaporation of the organic solvent can be crystallized directly from alcoholic solvents. In other cases crystallization is preceded by standard column chromatography methods.

Deprotection of the alkylated pyrrolones (c) follows standard methodology appropriate for the specific protecting group. For example, when R' is benzyl deprotection can be accomplished by catalytic hydrogenolysis employing, for example, hydrogen gas at pressures of approximately 20 psi with palladium on charcoal catalyst in an alcoholic solvent at temperatures of approximately 20° C. for about 30 minutes to about 2 hours.

When R' is para-methoxyphenyl, ceric ammonium nitrate in water is added to a suspension of (c) in acetonitrile and the mixture is stirred for 10 min to 1 hour while at −5° C. to 20° C. Sodium sulfite is then added with stirring for approximately 30 minutes, followed by the addition of solid sodium bicarbonate. The deprotected product (d) can be extracted from the aqueous mixture using, e.g., methylene chloride or ethyl acetate. Standard chromatography and crystallization methods are used to purify (d).

To displace the fluorine atom present in (d) with the various imidazole groups, it is convenient to first nitrate the aromatic ring. This is accomplished by standard nitration methods common to the art such as treatment with nitric acid - sulfuric acid. The nitro intermediates (e) can be precipitated from the reaction mixture by adding water and then recrystallized from alcoholic solvents. Displacement of fluorine is accomplished by combining (e) and 1 to 1.5 equivalents of the (optionally substituted) imidazole in a high boiling organic solvent such as dimethylformamide or dimethylsulfoxide, the later being a preferred solvent for the reaction. The mixture is placed under a nitrogen atmosphere and heated from 30° C. to 80° C. for 1 to 8 hours. The product (f) is isolated by adding water and cooling to approximately 0°–5° C. to cause precipitation. The crude product can be chromatographed or recrystallized to effect further purification.

When the groups $R_2$ and $R_3$ of the imidazole reactant reagent are the same (both H, or both the same lower alkyl), a single product is formed. If one of these groups is H and the other is lower alkyl, then the product (f) has $R_2=H$ and $R_3=$alkyl; only traces of the other isomer ($R_2=$alkyl, $R_3=H$) are formed. If the groups $R_2$ and $R_3$ in the imidazole reactant are different lower alkyl groups, then two isomeric products are formed: product (f) as shown in Scheme A, and product (f) with substituents $R_2$ and $R_3$ interchanged. In general the proportions of these isomers reflects the size of the two alkyl groups, the product with the smaller group in the $R_2$ position predominating. In this last case, the two isomers of (f) may be separated by, for example, crystallization or chromatography, and the separated isomers further transformed as described below. Alternatively, the mixture can be used directly in the later steps, and the isomers separated when convenient. The identification of the isomers is carried out with the aid of nuclear magnetic resonance spectroscopy.

The nitro group in (f) is removed by reduction to an amine followed by treatment with sodium nitrite and hypophosphorous acid employing methods known in the art. For instance, the reduction can be accomplished by either standard catalytic hydrogenation methodology or by the use of metal reducing agents such as tin (II) chloride employing an alcoholic solvent. Subsequent removal of the amino substituent typically involves addition of 1 to 1.5 equivalents of sodium nitrite to a solution of the amine intermediate in hydrochloric acid and aqueous hypophosphorous acid at 0° C. to 10° C. The addition of trace or catalytic amounts of copper (I) oxide is also beneficial for the reaction, which is allowed to proceed for 30 min to 2 hours at about 0° C. to 10° C. The products are separated by partitioning into n-butanol after neutralizing the reaction mixture with an inorganic base such as sodium carbonate. The n-butanol is evaporated and the products are further purified employing standard chromatography and crystallization techniques. The compounds, as their free bases, are typically solids with high melting points. If desired, crystalline acid addition salts can be prepared. For instance, treatment of the free base dissolved in an organic solvent such as methanol with an excess of an inorganic acid such as hydrogen chloride gas or methanolic hydrogen chloride, or approximately 1 equivalent of any common pharmaceutically acceptable organic acid such as methanesulfonic acid generates stable salts which can be recrystallized from organic solvents such as methanol-ether.

The preparation of the required starting materials (a) can be accomplished in two steps employing reactions as illustrated in Scheme B:

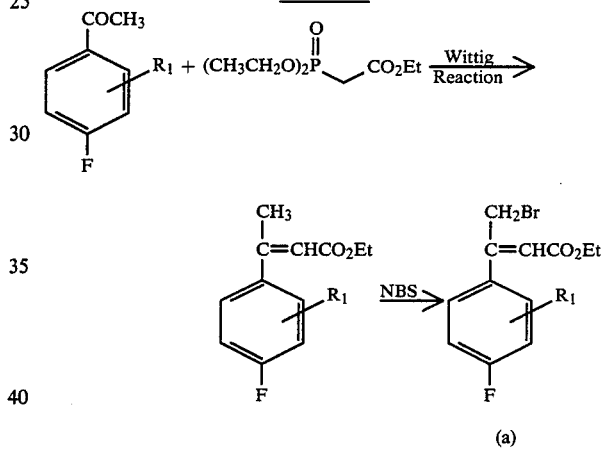

(a)

The first step utilizes common Wittig reaction conditions wherein triethyl phosphonoacetate is first deprotonated with sodium ethoxide in ethanol and an equimolar amount of the substituted acetophenone is then added. The mixture is heated to reflux for 10 to 24 hours and then the solvent is removed. After partitioning between an organic solvent and water, the product from the organic phase is distilled to effect purification. Only the desired trans isomer is formed in this step. Bromination of this material is conveniently effected by treatment with 1 equivalent of N-bromosuccinimide and catalytic benzoyl peroxide in carbon tetrachloride. The mixture is exposed to a heat-lamp and heated to reflux for two to six days. The product (a) can be isolated by partitioning between an organic solvent and water and purified by distillation after evaporation of the organic phase. Again, only the desired trans isomer is formed.

In the preparation of compounds of Formula I, the transformation of (b) into (c) (Scheme A) produces small amounts of by-products of the following formula (c').

this invention may be prepared as in the following Scheme C.

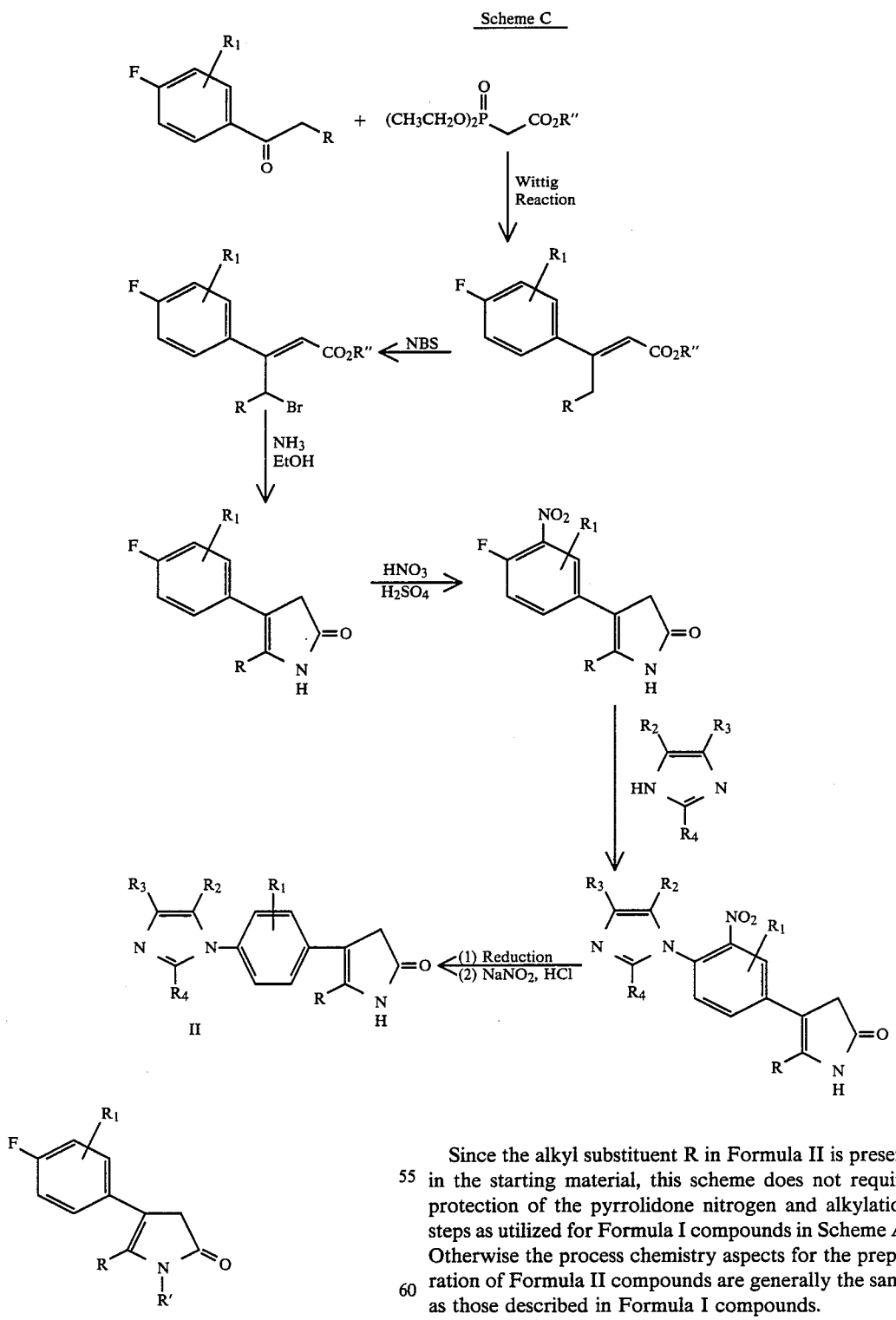

This by-product may be separated and purified by, e.g., chromatography and subsequently converted to compounds of Formula II by procedures analogous to those of Scheme A. It is more productive, however, to employ a process which gives compounds of Formula II exclusively. In general, compounds of Formula II of this invention may be prepared as in the following Scheme C.

Since the alkyl substituent R in Formula II is present in the starting material, this scheme does not require protection of the pyrrolidone nitrogen and alkylation steps as utilized for Formula I compounds in Scheme A. Otherwise the process chemistry aspects for the preparation of Formula II compounds are generally the same as those described in Formula I compounds.

METHOD-OF-USE AND PHARMACEUTICAL COMPOSITION ASPECT

The imidazolylphenylpyrrol-2-ones of this invention and their pharmaceutically acceptable acid addition salts as disclosed in general Formulae I and II may be used for the treatment of certain cardiovascular conditions, especially the treatment of congestive heart failure, wherein they act as cardiotonic agents. Additionally, they may be used in the treatment of any other condition which requires the strengthening of the heart action with a cardiotonic. Certain of the compounds of Formulae I and II might be expected to have other medically useful properties such as antiarrhythmic, antithrombotic, platelet aggregation inhibition, antihypertensive and bronchodilator actions.

Most generally, however, the compounds of this invention find their usefulness as cardiotonic agents. Their utility as cardiotonic agents may be determined in isolated cat or ferret pappilary muscle, using standard isometric recording techniques. Further testing is conducted by administering the compound (0.03–10 mg/kg) to be tested intravenously, orally or intraduodenally in a suitable vehicle, to dogs which have been anesthetized and instrumented for routine hemodynamic recordings, including the establishment of arterial and venous lines, the introduction of a left ventricular catheter for the measurement of left ventricular pressure and its first derivative (dp/dt), and suitable blood flow probes to determine aortic and coronary blood flow. Acute heart failure can be induced by sequential ligation of branches of the left coronary arteries, until left verticular and diastolic pressure exceeds 15 mm Hg.

In general, the compounds of this invention may be administered orally or parenterally. The dosage administered will be dependent on the mammalian host being treated, the route of administration and the magnitude and type of cardiotonic effect to be elicited.

For oral or parenteral administration the effective cardiotonic dose of the compounds of this invention for example 3-ethyl-1,5-dihydro-4-[4-(2-methyl-1H-imidazol-1-yl)phenyl]-2H-pyrrol-2-one ranges from about 0.001 mg/kg of body weight to about 30 mg/kg of body weight. Repetitive dosing may be required to achieve the appropriate positive inotropic effect for 24 hours.

For oral administration the compound to be administered can be formulated by admixing with any number of suitable pharmaceutical diluents and carriers such as lactose, sucrose, starch powder, cellulose, calcium sulfate, sodium benzoate and the like. Such formulations can be compressed into tablets or encapsulated into gelatin capsules for conventional oral administration. For parenteral administration a compound of this invention can be formulated, for example, for intramuscular or intravenous administration. Such parenteral administration formulations can be accomplished with any of a number of pharmaceutically acceptable carriers and diluents to constitute an injectable liquid solution. Commonly used diluents and carriers include water or saline solutions, and buffered aqueous solutions including dispersing and surface active agents, if necessary.

Thus, there is provided by this invention a method of eliciting a cardiotonic effect in a mammalian host having a disease condition in which therapeutic benefit is derived from elicitation of a cardiotonic effect which comprises administering to said host a non-toxic cardiotonically effective amount of the compound of this invention admixed with a pharmaceutically inert carrier. The invention described herein above is illustrated below in the Preparations and Examples, which however is not to be construed as limiting the scope of this invention.

PREPARATION 1

Ethyl 3-(4-Fluorophenyl)-2-butenoate

Triethyl phosphonoacetate (700 g, 3.1 mol) is added to sodium ethoxide (from sodium, 79 g, 3.4 mol in ethanol, 2.4 L) and the mixture is stirred for 15 minutes. 4-Fluoroacetophenone (431 g, 3.1 mol) is added, and the mixture is heated at reflux for 18 hr. The reaction mixture is evaporated, dissolved in ether, and washed with water and brine. The ethereal solution is dried with magnesium sulfate, filtered and evaporated. The residue is distilled to provide the title compound at 135°–140° C. (0.1 torr).

NMR (CDCl$_3$): $\delta$=1.31(t,3H), 2.56(d,3H), 4.21(quar,2H), 6.09(quar,1H), 7.05(t,2H), 7.45(dd,2H).

PREPARATION 2

Ethyl 4-Bromo-3-(4-fluorophenyl)-2-butenoate

Ethyl 3-(4-fluorophenyl)-2-butenoate (548 g, 2.7 mol), N-bromosuccinimide (500 g, 2.8 mol) and benzoyl peroxide (6 g) are combined in carbon tetrachloride (4 L). The mixture is heated at reflux and irradiated with a UV lamp for 4 days. The mixture is then filtered and the filtrate evaporated, and the residue is dissolved in ether and washed five times with saturated aqueous sodium carbonate and once with brine. The ether layer is dried with magnesium sulfate and evaporated, to provide the title compound.

NMR (CDCl$_3$): $\delta$=1.30(t,3H), 4.25(quar,2H), 4.90(s,2H), 6.10(s,1H), 7.05(t,2H), 7.50(dd,2H).

PREPARATION 3

4-(4-Fluorophenyl)-1,5-dihydro-1-(4-methoxyphenyl)-2H-pyrrol-2-one p-Anisidine (1793 g, 14.6 mol) and ethyl 4-bromo-3-(4-fluorophenyl)-2-butenoate (1393 g, 4.9 mol) are combined in ethanol (6 L), and the mixture is stirred for 24 hr. The precipitate which forms is collected by filtration, washed with ethanol, and dried under vacuum for 24 hr at 60° C. to give the title compound.

NMR (CDCl$_3$): $\delta$=3.82(s,3H), 4.74(s,2H), 6.70(s,1H), 6.96(d,2H), 7.18(t,2H), 7.58(dd,2H), 7.68(d,2H).

PREPARATION 4

3-Ethyl-4-(4-fluorophenyl)-1,5-dihydro-1-(4-methoxyphenyl)-2H-pyrrol-2-one

Lithium diisopropylamide is generated from diisopropylamine (122 mL, 0.87 mol) and n-butyllithium (2.5 M in hexane, 348 mL, 0.87 mol) in tetrahydrofuran (1.5 L) under a nitrogen atmosphere at −60° C., and 4-(4-fluorophenyl)-1,5-dihydro-1-(4-methoxyphenyl)-2H-pyrrol-2-one (235 g, 0.83 mol) is added to this mixture. The mixture is stirred for 30 minutes at −50° C., 1 hr at 0° C., and then re-cooled to −60° C. Ethyl iodide (73 mL, 0.91 mol) is added, and the reaction is allowed to warm slowly to 25° C., and stirred at this temperature for 18 hr. The mixture is poured into 1.5 L of 4 N HCl and stirred for 1 hr. The mixture is then extracted with methylene chloride, and the extracts are dried with magnesium sulfate and evaporated. Recrystallization of the residue from ethanol followed by drying under vacuum at 60° C. for 18 hr gives the title compound.

NMR (CDCl$_3$): $\delta$=1.23(t,3H), 2.56(quar,2H), 3.82(s,3H), 4.56(s,2H), 6.96(d,2H), 7.20(t,2H), 7.48(m,2H), 7.70(d,2H).

PREPARATION 5

4-(4-Fluorophenyl)-1,5-dihydro-1-(4-methoxyphenyl)-3-methyl-2H-pyrrol-2-one

In a manner similar to that described in Preparation 4, 4-(4-fluorophenyl)-1,5-dihydro-1-(4-methoxyphenyl)-2H-pyrrol-2-one is reacted with methyl iodide to give the title compound.

NMR (CDCl$_3$): $\delta$=2.14(t,3H), 3.82(s,3H), 4.57(quar,2H), 6.94(dd,2H), 7.18(ddd,2H), 7.50(ddd,2H), 7.69(dd,2H).

PREPARATION 6

3-Ethyl-4-(4-fluorophenyl)-1,5-dihydro-2H-pyrrol-2-one

A solution of ceric ammonium nitrate (542 g, 0.99 mol) in water (1L) is added dropwise over 45 minutes to a suspension of 3-ethyl-4-(4-fluorophenyl)-1,5-dihydro-1-(4-methoxyphenyl)-2H-pyrrol-2-one (103 g, 0.33 mol) in acetonitrile (2 L), while the temperature of the reaction mixture is maintained at 0°–10° C. After stirring 30 minutes sodium sulfite (125 g) is added. The mixture is stirred 30 minutes more and sodium bicarbonate (83 g) is added. After stirring an additional 30 minutes the mixture is concentrated to 1L and extracted with methylene chloride and ethyl acetate. The extracts are dried with magnesium sulfate, evaporated, and recrystallized from ethanol. Chromatography of this material on silica gel followed by drying under vacuum at 60° C. for 18 hr affords the title compound.

NMR (DMSO-d$_6$): $\delta$=1.06(t,3H), 2.38 (quar,2H), 4.20(s,2H), 7.36(m,2H), 7.60(m,2H), 8.32(s,1H).

PREPARATION 7

4-(4-Fluorophenyl)-1,5-dihydro-3-methyl-2H-pyrrol-2-one

In a manner similar to that described in Preparation 6, 4-(4-fluorophenyl)-1,5-dihydro-1-(4-methoxyphenyl)-3-methyl-2H-pyrrol-2-one is reacted to provide the title compound.

NMR (CDCl$_3$ ): $\delta$=2.08(t,3H), 4.24(s,2H), 7.06(brs,1H), 7.17(ddd,2H), 7.48(ddd,2H).

PREPARATION 8

3-Ethyl-4-(4-fluoro-3-nitrophenyl)-1,5-dihydro-2H-pyrrol-2-one

Nitric acid (70%, 14 mL, 0.22 mol) is added dropwise to a solution of 3-ethyl-4-(4-fluorophenyl)-1,5-dihydro-2H-pyrrol-2-one (37.6 g, 0.18 mol) in concentrated sulfuric acid (140 mL) while the temperature is maintained at 0°–5° C. The mixture is stirred for 2 hr at 0° C., and then is poured onto 2500 g of ice. The resulting precipitate is collected by filtration, and washed with water until the washes are neutral. Recrystallization of the solid from ethanol followed by drying under vacuum at 50° C. for 24 hr provides the title compound.

NMR (DMSO-d$_6$): $\delta$=1.10(t,3H), 2.42(quar,2H), 4.30(s,2H), 7.76(dd,1H), 7.98(m,1H), 8.26(dd,1H), 8.48(s,1H).

PREPARATION 9

4-(4-Fluoro-3-nitrophenyl)-1,5-dihydro-3-methyl-2H-pyrrol-2-one

In a manner similar to that described in Preparation 8, 4-(4-fluorophenyl)-1,5-dihydro-3-methyl-2H-pyrrol-2-one is reacted with nitric acid to provide the title compound.

NMR (DMSO-d$_6$): $\delta$=1.96(s,3H), 4.27(d,2H), 7.75(dd,1H), 7.95–8.00(m,1H), 8.25(dd,1H), 8.48(s,1H).

PREPARATION 10

1,5-Dihydro-3-methyl-4-[4-(2-methyl-1H-imidazol-1-yl)-3-nitrophenyl]-2H-pyrrol-2-one 4-(4-Fluoro-3-nitrophenyl)-1,5-dihydro-3-methyl-2H-pyrrol-2-one (6.5g, 28 mmol) and 2-methylimidazole (6.8 g, 83 mmol) are combined in dimethylsulfoxide (50 mL) and the mixture is heated to 50° C. under a nitrogen atmosphere for 4 hr. The mixture is then cooled to room temperature, and water is added to give a precipitate. The mixture is kept cold for 1 hr, and the precipitate is collected by filtration, washed with water, and air-dried to provide the title compound.

NMR (DMSO-d$_6$): $\delta$=2.03(s,3H), 2.16(s,3H), 4.36(s,2H), 6.98(d,1H), 7.28(d,1H), 7.87(d,1H), 8.07(dd,1H), 8.36(d,1H), 8.57(s,1H).

PREPARATION 11

1,5-Dihydro-4-[4-(1H-imidazol-1-yl)-3-nitrophenyl]-3-methyl-2H-pyrrol-2-one

In a manner similar to that described in Preparation 10, 4-(4-fluoro-3-nitrophenyl)-1,5-dihydro-3-methyl-2H-pyrrol-2-one is reacted with imidazole to provide the title compound.

NMR (DMSO-d$_6$):$\delta$=2.02(s,3H), 4.36(s,2H), 7.17(s,1H), 7.52(s,1H), 7.86(d,1H), 8.01(s,1H), 8.05(dd,1H), 8.36(d,1H), 8.56(s,1H).

PREPARATION 12

In a manner similar to that described in Preparation 10, 3-ethyl-4-(4-fluoro-3-nitrophenyl)-1,5-dihydro-2H-pyrrol-2-one is reacted with the following reactants respectively:
(a) imidazole,
(b) 2-methylimidazole, to produce the following products respectively:
(c) 3-ethyl-1,5-dihydro-4-[4-(1H-imidazol-1-yl)-3-nitrophenyl]-2H-pyrrol-2-one,
(d) 3-ethyl-1,5-dihydro-4-[4-(2-methyl-1H-imidazol-1yl)-3-nitrophenyl]-2H-pyrrol-2-one.

PREPARATION 13

4-[3-Amino-4-(2-methyl-1H-imidazol-1-yl)phenyl]-1,5-dihydro-3-methyl-2H-pyrrol-2-one 1,5-Dihydro-3-methyl-4-[4-(2-methyl-1H-imidazol-1-yl)-3-nitrophenyl]-2H-pyrrol-2-one (7.3 g, 24 mmol) and tin (II) chloride dihydrate (28 g, 125 mmol) are combined in ethanol (330 mL), and the mixture is heated at reflux under a nitrogen atmosphere for 30 minutes. The mixture is cooled, made basic with saturated aqueous sodium bicarbonate, and filtered through celite. The filter cake is washed with ethanol, and the filtrates are evaporated. Chromatography of the residue on alumina provides the title compound.

NMR (DMSO-d$_6$):δ=1.95(t,3H), 2.13(s,3H), 4.15(br s,2H), 5.00(br s,2H), 6.70–7.10 (m,5H), 8.25(br s,1H).

PREPARATION 14

In a manner similar to that described in Preparation 13, tin (II) dichloride dihydrate is reacted with the following reactants respectively:
(a) 1,5-dihydro-4-[4-(1H-imidazol-1-yl)-3-nitrophenyl]-3-methyl-2H-pyrrol-2-one,
(b) 3-ethyl-1,5-dihydro-4-[4-(1H-imidazol-1-yl)-3-nitrophenyl]-2H-pyrrol-2-one,
(c) 3-ethyl-1,5-dihydro-4-[4-(2-methyl-1H-imidazol-1-yl)-3-nitrophenyl]-2H-pyrrol-2-one,
to produce the following products respectively:
(d) 4-[3-amino-4-(1H-imidazol-1-yl)phenyl]-1,5-dihydro-3-methyl-2H-pyrrol-2-one,
(e) 4-[3-amino-4-(1H-imidazol-1-yl)phenyl]-3-ethyl-1,5-dihydro-2H-pyrrol-2-one,
(f) 4-[3-amino-4-(2-methyl-1H-imidazol-1-yl)phenyl]-3-ethyl-1,5-dihydro-2H-pyrrol-2-one.

EXAMPLE I

3-Ethyl-1,5-dihydro-4-[4-(2-methyl-1H-imidazol-1-yl)phenyl]-2H-pyrrol-2-one

4-[3-Amino-4-(2-methyl-1H-imidazol-1-yl)phenyl]-3-ethyl-1,5-dihydro-2H-pyrrol-2-one (2.0 g, 7.1 mmol) is dissolved in concentrated HCl (40 mL) at 5° C, and hypophosphorous acid (50% aqueous solution, 14.6 mL, 0.14 mol) is added dropwise. Aqueous sodium nitrite (2 N, 4.4 mL, 8.8 mmol) is added, and the mixture is stirred for 5 minutes. A trace amount of copper (I) oxide is added, and the mixture is stirred an additional 1 hr at 5° C. The mixture is neutralized with sodium carbonate, extracted with n-butanol, and the extracts are evaporated. The residue is triturated with methanol, filtered, and the filtrates are evaporated. Chromatography of the residue on silica gel followed by recrystallization from ethanol and drying under vacuum at 70° C. for 18 hr provides the title compound.

NMR (DMSO-d$_6$): δ=1.10(t,3H), 2.32(s,3H), 2.42(quar,2H), 4.26(s,2H), 6.96(s,1H), 7.37(s,1H), 7.58(d,2H), 7.66(d,2H), 8.40(s,1H).

EXAMPLE II

In a manner similar to that described in Example I, the following reactants, respectively:
(a) 4-[3-amino-4-(1H-imidazol-1-yl)phenyl]-3-ethyl-1,5-dihydro-2H-pyrrol-2-one,
(b) 4-[3-amino-4-(1H-imidazol-1-yl)phenyl]-1,5-dihydro-3-methyl-2H-pyrrol-2-one,
(c) 4-[3-amino-4-(2-methyl-1H-imidazol-1-yl)phenyl]-1,5-dihydro-3-methyl-2H-pyrrol-2-one,
(d) 4-[3-amino-4-(1H-imidazol-1-yl)phenyl]-1,3-dihydro-5-methyl-2H-pyrrol-2-one,
(e) 4-[3-amino-4-(2-methyl-1H-imidazol-1-yl)phenyl]-1,3-dihydro-5-methyl-2H-pyrrol-2-one,
are converted to the following products, respectively:
(f) 3-ethyl-1,5-dihydro-4-[4-(1H-imidazol-1-yl)phenyl]-2H-pyrrol-2-one,
(g) 1,5-dihydro-4-[4-(1H-imidazol-1-yl)phenyl]-3-methyl-2H-pyrrol-2-one,
(h) 1,5-dihydro-3-methyl-4-[4-(2-methyl-1H-imidazol-1-yl)phenyl]-2H-pyrrol-2-one,
(i) 1,3-dihydro-4-[4-(1H-imidazol-1-yl)phenyl]-5-methyl-2H-pyrrol-2-one,
(j) 1,3-dihydro-5-methyl-4-[4-(2-methyl-1H-imidazol-1-yl)phenyl]-2H-pyrrol-2-one.

EXAMPLE III

3-Ethyl-1,5-dihydro-4-[4-(1H-imidazol-1-yl)phenyl]-2H-pyrrol-2-one Hydrochloride A 0.253 g (1 mmol) quantity of compound from Example II is dissolved in 5 mL of ethanol. To this solution is added 5 mL of saturated ethanolic HCl. The solution is evaporated under reduced pressure to a volume of 3 mL and then is kept at −15° C. for ten hours. The resulting crystals are collected by filtration to provide the title compound.

NMR (DMSO-D$_6$): δ=1.08(t,3H), 2.49(quar, 2H), 4.25(s,2H), 7.75(d,2H), 7.92(d,2H), 7.94(s,1H), 8.33(s,1H), 8.34(s,1H), 9.78(s,1H).

We claim:
1. A compound of one of the following Formulae:

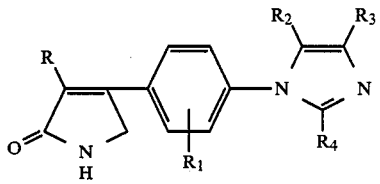

and

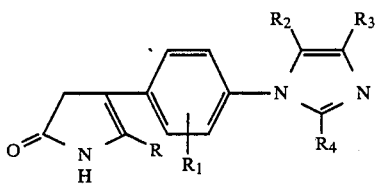

wherein
R is lower alkyl;
R$_1$, R$_2$, R$_3$ and R$_4$ are the same or independently hydrogen or lower alkyl, or R$_2$ and R$_3$ taken together form a benzene ring;
or a pharmaceutically acceptable acid addition salt thereof;
with the proviso that R cannot be tertiary butyl.

2. A compound of claim 1, Formula I wherein R$_1$, R$_2$, R$_3$ and R$_4$ are hydrogen.

3. A compound of claim 1, Formula I wherein R$_4$ is lower alkyl and R$_1$, R$_2$ and R$_3$ are hydrogen.

4. A compound of claim 2 which is 1,5-dihydro-4-[4-(1H-imidazol-1-yl)phenyl]-3-methyl-2H-pyrrol-2-one.

5. A compound of claim 2 which is 3-ethyl-1,5-dihydro-4-[4-(1H-imidazol-1-yl)phenyl]-2H-pyrrol-2-one.

6. A compound of claim 3 which is 1,5-dihydro-3-methyl-4-[4-(2-methyl-1 H-imidazol-1-yl)phenyl]-2H-pyrrol-2-one.

7. A compound of claim 3 which is 3-ethyl-1,5-dihydro-4-[4-(2-methyl-1H-imidazol-1-yl)phenyl]-2H-pyrrol-2-one.

8. A compound of claim 1, Formula II, which is 1,3-dihydro-4-[4-(1H-imidazol-1-yl)phenyl]-5-methyl-2H-pyrrol-2-one.

9. A compound of claim 1, Formula II which is 1,3-dihydro-5-methyl-4-[4-(2-methyl-1H-imidazol-1-yl)phenyl]-2H-pyrrol-2-one.

10. A compound of claim 1, Formula II which is 5-ethyl-1,3-dihydro-4-[4-(2-methyl-1H-imidazol-1-yl)phenyl]-2H-pyrrol-2-one.

11. A compound of claim 1, Formula II which is 5-ethyl-1,3-dihydro-4-[4-(1H-imidazol-1-yl)phenyl]-2H-pyrrol-2-one.

12. A pharmaceutical composition for treating cardiac failure comprising a non-toxic cardiotonically effective amount of a compound of claim 1 in admixture with a non-toxic pharmaceutically acceptable carrier.

13. The method of treating cardiac failure in a mammalian host having a disease condition in which therapeutic benefit is derived from elicitation of a cardiotonic effect which comprises administering to said host a non-toxic cardiotonically effective amount of a compound of claim 1.

* * * * *

UNITED STATES PATENT AND TRADEMARK OFFICE
CERTIFICATE OF CORRECTION

PATENT NO. : 4,737,511

DATED : April 12, 1988

INVENTOR(S) : Paul W. Erhardt, Alfred A. Hagedorn, III and John W. Lampe

It is certified that error appears in the above-identified patent and that said Letters Patent is hereby corrected as shown below:

Column 2, line 32 "-imidazol-1yl)phenyl]" should read
.... imidazol-1-yl)phenyl] ....

Column 2, line 39 "-imidazol-1yl)phenyl" should read
.... -imidazol-1-yl)phenyl ....

Column 4, line 44 "raised to between -20°C and -30°C"
should read .... raised to between 20°C and 30°C ....

Column 12, line 60 "(2-methyl-1H-imidazol-1yl)" should read
.... (2-methyl-1H-imidazol-1-yl) ....

Column 14, line 18 "II is dissolved" should read
.... IIf is dissolved ....

Column 14, line 67 "[4-(2-methyl-11 H-imidazol" should read
.... [4-(2-methyl-1H-imidazol ....

Signed and Sealed this

Ninth Day of May, 1989

*Attest:*

DONALD J. QUIGG

*Attesting Officer*     *Commissioner of Patents and Trademarks*